United States Patent [19]

Takahashi et al.

[11] Patent Number: 5,441,535
[45] Date of Patent: Aug. 15, 1995

[54] BLOOD PUMP

[75] Inventors: Katsumi Takahashi; Hiroshi Sasagawa, both of Koga, Japan

[73] Assignee: Urawa Kohgyo Co., Ltd., Kuki, Japan

[21] Appl. No.: 150,878

[22] Filed: Nov. 12, 1993

[30] Foreign Application Priority Data

Nov. 27, 1992 [JP] Japan ................... 4-339526

[51] Int. Cl.$^6$ ............... A61M 1/10; F03B 13/00; F04D 7/00
[52] U.S. Cl. ................... 623/3; 415/900; 416/223 B
[58] Field of Search ............... 623/3; 600/16; 415/170.1, 900; 416/223 B; 216/782, 783, 321.63

[56] References Cited

U.S. PATENT DOCUMENTS

| | | | |
|---|---|---|---|
| 3,961,867 | 6/1976 | Woollenweber | 417/407 |
| 4,599,081 | 7/1986 | Cohen | 623/2 |
| 4,643,641 | 2/1987 | Clausen et al. | 415/170 |
| 5,145,333 | 9/1992 | Smith | 417/405 |
| 5,147,187 | 9/1992 | Ito et al. | 417/423.1 |
| 5,316,440 | 5/1994 | Kijima et al. | 415/206 |

FOREIGN PATENT DOCUMENTS 861142 7/1949 Germany .............. 416/223 B
84596 3/1957 Netherlands .............. 416/223 B Primary Examiner—David Isabella
Assistant Examiner—Laura Fossum
Attorney, Agent, or Firm—Oblon, Spivak, McClelland, Maier & Neustadt

[57] ABSTRACT

A blood pump for circulating blood by a rotor rotating in a space of a casing which is formed substantially in a flat shape and has a suction port and a discharge port, comprises a conical projecting portion provided at the central portion of the rotor, and a blade body formed continuously to a vicinity of the outer periphery of the base portion of the projecting portion, in which upper side recessed passages and lower side passages are alternately and radially formed. Base portions of the upper side recessed passages and the lower side passages are interconnected to each other by communicating passages. With this blood pump, the passages for blood are formed at either of the upper and lower gaps between the rotor and the casing, so that blood is transferred to the outer peripheral portion, thus preventing the solidification of the blood due to the stagnation thereof. This makes it possible to eliminate the problem in causing the thrombus of the peripheral blood vessels by the solidified blood permeating in the body, and in exerting adverse effects on the kidney.

7 Claims, 3 Drawing Sheets

BLOOD PUMP

BACKGROUND OF THE INVENTION

1. Field of the Invention

The present invention relates to a blood pump for forcibly circulating blood, which is used in decay of a patient's heart or in an operation thereof.

2. Description of the Related Art

Conventionally, there has been known such a blood pump as shown in FIG. 6. In this blood pump, inclined strip-like long and short blades b and c are alternately and radially formed on the upper surface of a disk-like rotor a, and a cavity d is formed in the rotor a at the position where the base portions of the blades b and c are located.

Additionally, in this figure, reference symbol e indicates a casing; f is a suction port; and g is a discharge port.

In the above conventional blood pump, however, a passage for allowing blood to forcibly flow down to a gap portion between the lower surface of the rotor a and the casing e, and for introducing the blood up to the outer peripheral portion of the rotor a is not formed, and accordingly, when blood or air stagnates at the gap portion, particularly, in the vicinity of the rotating shaft of the rotor a, there occurs solidification of the blood at this portion.

The blood thus solidified is pushed out by the blades, and enters in the body from the discharge port g. This brings about disadvantages in causing the thrombus of the peripheral blood vessels, and in exerting adverse effects on the kidney.

SUMMARY OF THE INVENTION

An object of the present invention is to prevent blood or air from stagnating to be solidified at a gap portion between a casing of a pump and a rotor rotating therein, and hence to suppress the thrombus of the peripheral blood vessels and the adverse effects exerted on the kidney.

Another object of the present invention is to prevent the leakage of blood from a pump section, and hence to increase the durability of a blood pump.

To achieve the above objects, according to the present invention, there is provided a blood pump for circulating blood by a rotor rotating in a space of a casing which is formed substantially in a flat shape and has a suction port and a discharge port, comprising: a conical projecting portion provided at the central portion of the rotor; and a blade body formed continuously to a vicinity of the outer periphery of the base portion of the projecting portion, in which upper side recessed passages and lower side passages are alternately and radially formed; wherein base portions of the upper side recessed passages and the lower side passages are interconnected to each other by communicating passages.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
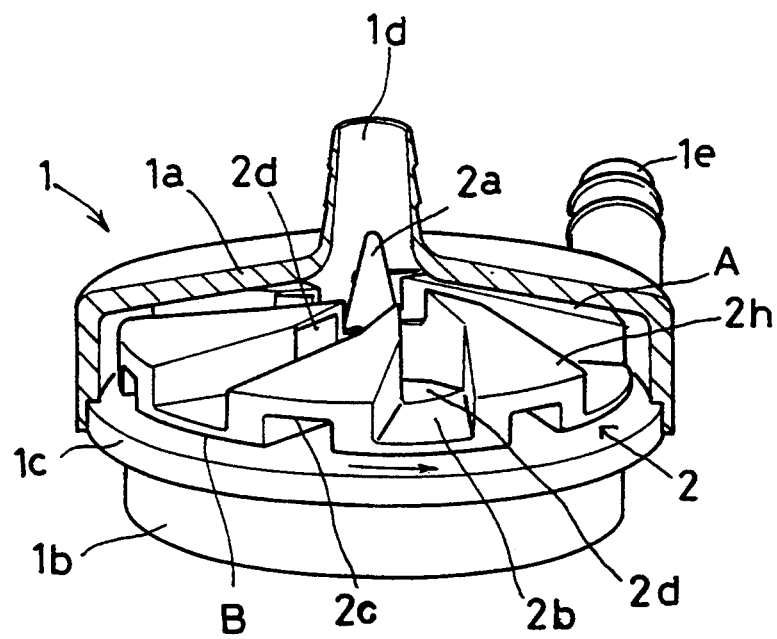
FIG. 1 is a perspective view of a first embodiment of the present invention, with parts partially cut-away.

Referring now to the drawings, wherein like reference numerals designate identical or corresponding parts throughout the several views, a first embodiment of the present invention will be described with reference to FIGS. 1 and 2.

Reference numeral 1 indicates a casing, which includes an upper casing 1a which is formed substantially in a flat shape with the upper surface inclined, a lower casing 1b formed in a tray-like shape, and a partitioning plate 1c interposed between the upper casing 1a and the lower casing 1b. In the upper casing 1a, a suction port 1d for blood is provided at the central upper surface and a discharge port 1e is provided on a side surface.

Reference numeral 2 indicates a rotor, which is fixed around a rotating shaft 3 and has a conical projecting portion 2a at its central portion. A blade body 2h is formed continuously to the outer periphery of the lower portion of the projecting portion 2a, in which upper side recessed passages 2b opened upwardly and lower recessed passages 2c opened downwardly are alternately and radially formed in a plurality of sets. These recessed passages 2b and 2c are interconnected to each other by communicating passages 2d at the base portions thereof.

Reference numeral 4 indicates a drive rotor, which is rotatably mounted around the rotating shaft 3 and has a magnet 4a, to be rotated by a drive coil (not shown).

Additionally, reference numeral 5 and 5 indicate bearings.

Next, the operation of the above embodiment will be described below.

Figure 2:
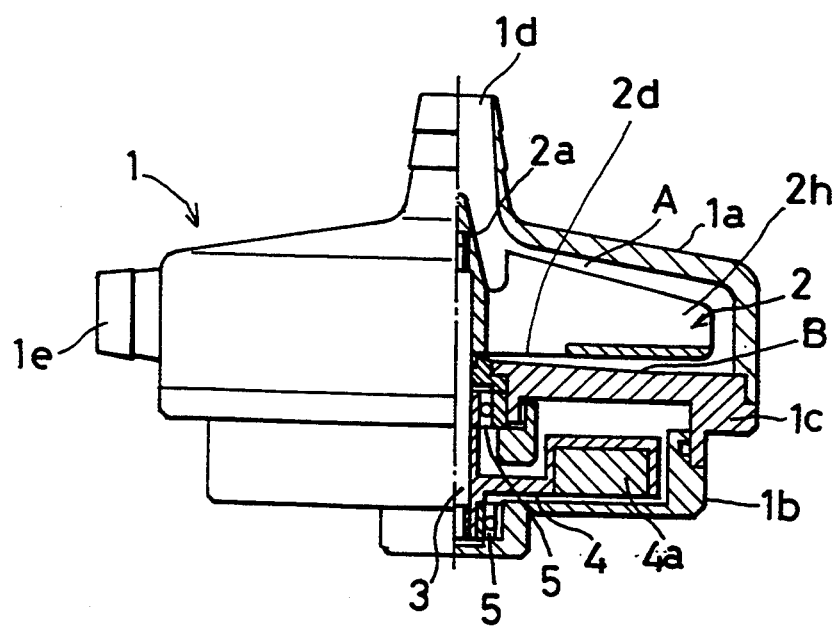
FIG. 2 is a front view of the first embodiment of the present invention, with parts partially cut-away.

As the rotor 2 is rotated in the direction of the arrow of FIG. 1 by the rotation of the drive rotor 4, the blood sucked from the suction port 1d is allowed to flow outwardly by the projecting portion 2a, and to flow in the direction of the outer periphery of the rotor 2 through the upper side recessed passages 2b by the centrifugal force. At the same time, the blood branched by the communicating passages 2d passes through the lower side recessed passages 2c and is allowed to flow in the direction of the outer periphery of the rotor 2, after which it is joined with the blood passing through the upper side recessed passages 2b, to be thus discharged from the discharge port 1e.

Accordingly, since the blood is pushed to usually flow outwardly to both a gap portion A between the rotor 2 and the upper casing 1a, and a gap portion B between the rotor 2 and the partitioning plate 1c, there never occurs the solidification of the blood due to stagnation thereof.

Figure 3:
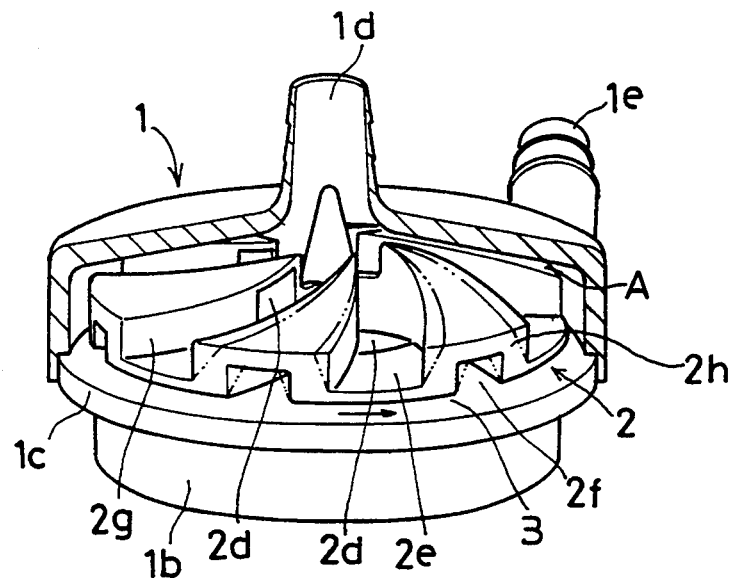
FIG. 3 is a perspective view of a second embodiment of the present invention, with parts partially cut-away.

FIG. 3 shows a second embodiment of the present invention. In this embodiment, the recessed passages 2b and 2c formed in linear shapes as shown in FIG. 1 are replaced by passages 2e and 2f formed in circular-arc shapes. Further, side surfaces 2g and 2g of the passages 2e and 2f are formed in perpendicular surfaces. Accordingly, in this embodiment, the flow-out of the blood from the passages to the outer peripheral space is made smooth, which prevents a turbulent flow.

Further, the perpendicular surface 2g may be inclined with respect to the rotational direction as shown in the dotted line, which achieves an effect of adding a forcible blood pressure to the gap portions A and B.

In addition, by suitably changing the widths of the recessed passages 2b and 2c or the sectional area of the communicating passage, for example, by reducing the sectional area of the communicating passage, enlarging the upper side recessed passage 2b and reducing the lower side recessed passage 2c, it is possible to adjust the flow rate of the blood flowing in the vertical direction of the rotor 2, and hence to suppress the breakage of the blood due to the turbulent flow generated by the rotation of the rotor 2.

Figure 4:
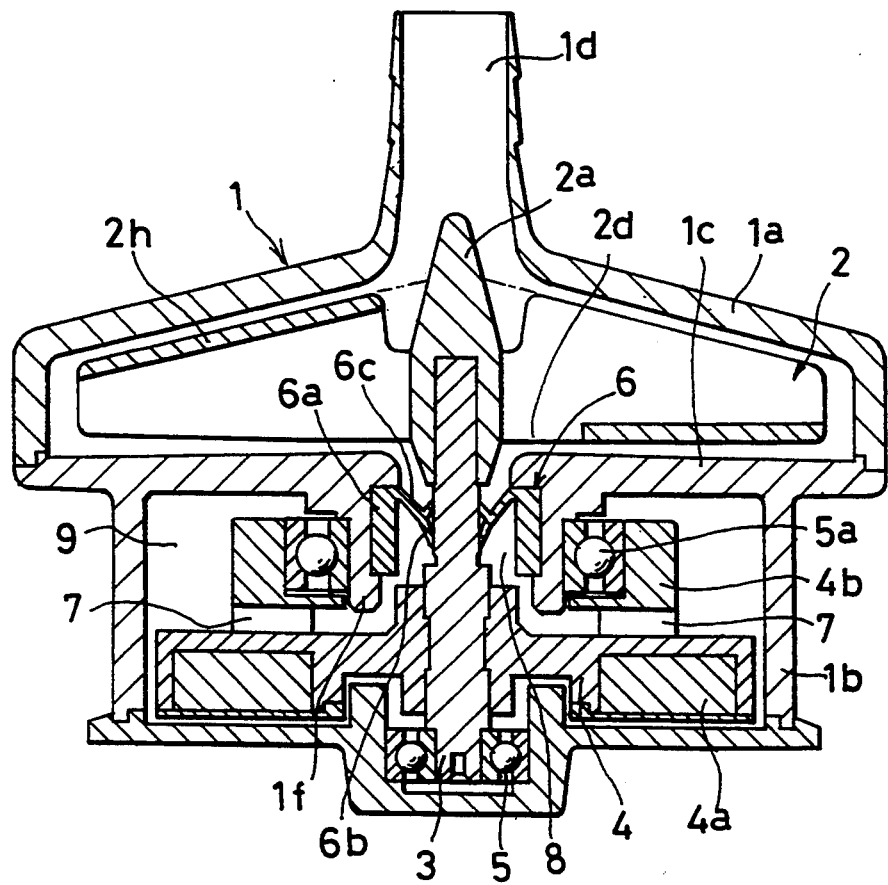
FIG. 4 is a sectional view of a third embodiment of the present invention.

FIG. 4 shows a third embodiment. In this embodiment, a supporting cylindrical body if is provided at the central portion of the partitioning plate 1c so as to project downward, and a short sized receiving cylindrical body 4b is projectingly provided on the upper surface of the drive rotor 4. Further, a seal means 6 is interposed between the outer surface of the rotating shaft 3 and the inner surface of the supporting cylindrical body 1f, and a bearing means 5a composed of a large sized bearing is interposed between the outer surface of the supporting cylindrical body if and the inner surface of the receiving cylindrical body 4b.

The above seal means 6 includes a cylindrical portion 6a press-contacted with the inner surface of the supporting cylindrical body 1f, a beer barrel shaped cylindrical seal portion 6b press-contacted with the outer surface of the rotating shaft 3, and a bell-like and elastic thin interlocking portion 6c for interlocking the end portion of the cylindrical portion 6a on the rotor 2 side with the intermediate portion of the outer periphery of the seal portion 6b.

Further, a plurality of radial through-holes 7 are radially formed on the receiving cylindrical body 4b, and the inner openings of the through-holes 7 are communicated with a space 8 formed by the cylindrical portion 6a of the seal means 6 and the interlocking portion 6c.

Thus, the rotating shaft 3 is supported by the large sized bearing means 5a provided at the outer position of the seal means 6, while the bearing means 5a is sufficiently apart from the bearing 5. This makes it possible to suppress the deflection of the rotating shaft 3 at minimum during the rotation of the rotor 2, and hence to ensure the stable rotation of the rotor 2. In addition, since the rotating shaft 3 is press-contacted with the seal portion 6b of the seal means 6 by the fastening force of the beer barrel shape of the seal portion 6a, and further, since the rotating shaft 3 is supported by the bell-like and elastic thin interlocking portion 6c so as to be freely eccentric in the radial direction, the rotor 2 is capable of extremely flexibly following the deflection of the rotating shaft. This makes it possible to prevent the leakage of the blood, and hence to increase the durability of the blood pump.

Further, even if the sliding surface of the seal portion 6b of the seal means 6 is worn for a long period of time and the blood leaked from the seal portion 6b is allowed to flow in the space 8, the blood in the space 8 is allowed to flow out from the through-holes 7 into the outer space 9 of the receiving cylindrical body 4b while by-passing the bearing means 5a through the centrifugal force generated by the rotation of the rotor 2, and stagnates thereat. Accordingly, it is possible to observe the flow-out blood through the transparent lower side casing 1b, and hence to prevent the flow-out blood from permeating in the bearing which leads to the breakage thereof and causes the serious trouble of stopping the pump. Therefore, the pump can be used with safety.

Figure 5:
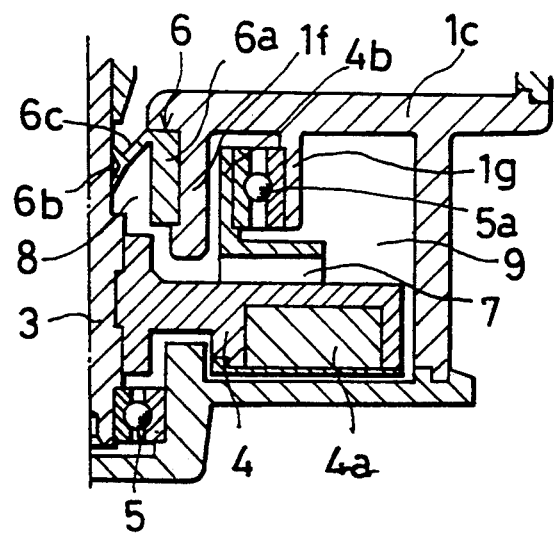
FIG. 5 is a sectional view of main parts of a fourth embodiment of the present invention.
Figure 6:
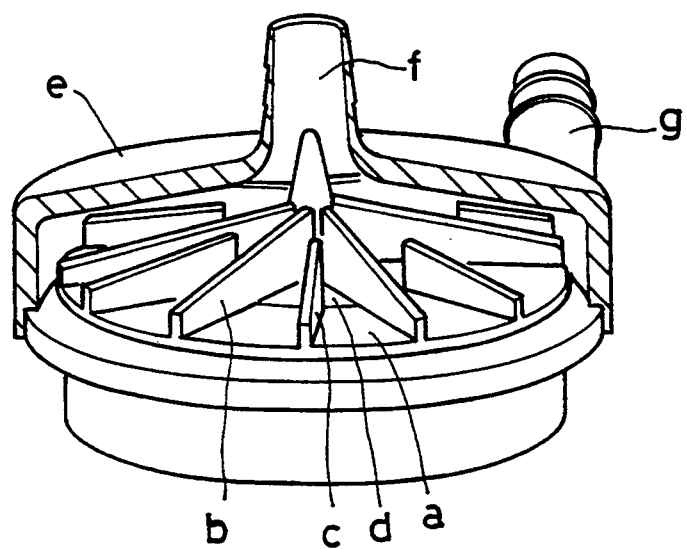
FIG. 6 is a perspective view of a conventional blood pump, with parts partially cut-away.

FIG. 5 shows a fourth embodiment, wherein the mounting portion of the bearing means 5a in the third embodiment is modified. Namely, an auxiliary supporting cylindrical body 1g is projectingly provided in addition to the partitioning plate 1c, and the receiving cylindrical body 4b from the drive rotor 4 is projectingly provided between the supporting cylindrical body if and the auxiliary supporting cylindrical body 1g. Further, the bearing means 5a is interposed between the outer surface of the receiving cylindrical body 4b and the inner surface of the auxiliary supporting cylindrical body 1g. The operation of this embodiment is the same as that of the third embodiment.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A blood pump for circulating blood by a rotor rotating in a space of a casing which is formed substantially in a flat shape and has a suction port and a discharge port, the blood pump comprising:
   a conical projecting portion provided at a central portion of said rotor;
   a blade body extending from an outer periphery of a base portion of said projecting portion, said blade body having upper side recessed passages and lower side passages which are alternately and radially formed on said blade body; and
   communicating passages formed on a radially inward portion of said blade body interconnecting said upper side recessed passages to said lower side recessed passages.

2. A blood pump according to claim 1, wherein said upper side recessed passages have sides which are formed linearly and perpendicularly to said blade body.

3. A blood pump according to claim 1, wherein said upper side recessed passages have sides formed in a circular-arc and are perpendicular to said blade body.

4. A blood pump according to claim 1, wherein said upper side recessed passages have sides formed in a circular-arc and are inclined with respect to said blade body.

5. A blood pump according to one of claims 1, 2, 3 or 4, wherein:
   the rotor comprises a rotating shaft, said rotating shaft being freely fitted in a supporting cylindrical body interlocked with said casing;
   a drive rotor having a receiving cylindrical body projectingly provided at a peripheral edge of the drive rotor is fixed at a base portion of said rotating shaft;
   a seal means is interposed between said rotating shaft and said supporting cylindrical body; and
   a large sized bearing means is interposed between said supporting cylindrical body and said receiving cylindrical body.

6. A blood pump according to claim 5, wherein:
said seal means comprises a cylindrical portion press-contacted with an inner surface of said supporting cylindrical body, a seal portion press-contacted with an outer periphery of said rotating shaft, and an elastic interlocking portion which extends between the cylindrical portion and the seal portion.

7. A blood pump according to claim 6, wherein a plurality of radial through-holes are formed on said receiving cylindrical body, said plurality of radial through-holes communicating with a space formed by the cylindrical portion and the interlocking portion of said seal means.

* * * * *